(12) United States Patent
Robran

(10) Patent No.: US 11,517,466 B2
(45) Date of Patent: Dec. 6, 2022

(54) LIMB ELEVATION DEVICE WITH SECUREMENT STRAPS

(71) Applicant: BONE FOAM, INC., Corcoran, MN (US)

(72) Inventor: Chad L. Robran, Plymouth, MN (US)

(73) Assignee: Bone Foam, Inc., Corcoran, MN (US)

( * ) Notice: Subject to any disclaimer, the term of this patent is extended or adjusted under 35 U.S.C. 154(b) by 23 days.

(21) Appl. No.: 17/095,220

(22) Filed: Nov. 11, 2020

(65) Prior Publication Data
US 2021/0186738 A1 Jun. 24, 2021

Related U.S. Application Data

(60) Provisional application No. 62/952,887, filed on Dec. 23, 2019.

(51) Int. Cl.
*A61F 5/37* (2006.01)
*A61G 13/12* (2006.01)
*A61G 7/10* (2006.01)

(52) U.S. Cl.
CPC .......... *A61F 5/3761* (2013.01); *A61F 5/3776* (2013.01); *A61G 7/1096* (2013.01); *A61G 13/1245* (2013.01)

(58) Field of Classification Search
CPC ... A61F 5/3761; A61F 5/3776; A61G 7/1096; A61G 13/1245; Y10S 482/907; A61B 6/04; A61B 6/4283; A61B 6/0421; A61B 50/20; A63B 21/00047; A63B 21/068; A63B 2208/0242; A63B 2208/0214; A63B 23/0233; A63B 2023/006; A63B 21/4015; A63B 2208/0252; A63B 2208/0295; A63B 2208/0238; A63B 2208/0247; A63B 23/03508; A63B 23/04; A63B 2022/0033; A63B 23/035; A63B 23/08; A63B 69/0062
USPC ......... 5/618, 624; 128/845; 602/23; 378/177
See application file for complete search history.

(56) References Cited

U.S. PATENT DOCUMENTS

| | | | | |
|---|---|---|---|---|
| 5,046,487 A | * | 9/1991 | Scott ................. | A63B 23/085 128/DIG. 15 |
| 5,147,267 A | * | 9/1992 | Kunewalder ...... | A63B 23/0233 482/142 |
| 5,687,742 A | * | 11/1997 | Johnson ............. | A61F 5/0585 606/240 |
| 6,634,045 B1 | * | 10/2003 | DuDonis ............ | A47C 20/021 5/632 |

\* cited by examiner

*Primary Examiner* — Ophelia A Hawthorne
(74) *Attorney, Agent, or Firm* — Workman Nydegger

(57) ABSTRACT

A limb elevation device comprising a base having a proximal section with an angled upper surface and a distal section with a planar upper surface. The bottom surface of the distal section having one or more recesses with anchor points disposed within the one or more recesses. Securement straps may be selectively attached to the anchor points and the securement straps may be utilized to secure the limb elevation device to a table, bed, or other surface and/or to secure the patient's leg to the securement device itself.

20 Claims, 10 Drawing Sheets

LIMB ELEVATION DEVICE WITH SECUREMENT STRAPS

CROSS-REFERENCE TO RELATED APPLICATIONS

This Application claims the benefit of U.S. Provisional Application No. 62/952,887, filed Dec. 23, 2019, which is incorporated by reference in its entirety.

BACKGROUND

Technical Field

This disclosure generally relates to limb elevation devices. More specifically, the present disclosure relates to limb elevation devices including limb stabilization features.

Related Technology

Limb elevation is beneficial in a number of treatment plans related to injured limbs. For example, it is often recommended that post-injury or post-surgery, a patient's leg should be elevated in order to maximize fluid drainage away from injured tissue, and to reduce swelling, pain and inflammation which can help the leg to recover faster. Elevation of the leg typically requires a patient to be in a sitting or lying position and then elevating the leg above the level of the patient's heart.

In order for the therapeutic effects of elevation of the leg to be effective, the leg may be required to remain elevated for an extended period of time. The devices currently available for leg elevation are cumbersome, heavy, and lack the proper combination of shape and material to support leg elevation for an extended period of time.

Accordingly, there are a number of disadvantages with limb elevation devices that can be addressed.

BRIEF SUMMARY

Implementations of the present disclosure solve one or more of the foregoing or other problems in the art with limb elevation devices. In particular, one or more implementations can include a limb elevation device comprising a base having a proximal section with an inclined upper surface, and a distal section with a substantially flat or planar upper surface.

Apparatuses of the present disclosure can also include one or more anchor points disposed and fixed within recesses on the bottom surface of the distal section of the base. Limb-securing straps, or securement straps, may be selectively attached to the anchor points.

This summary is provided to introduce a selection of concepts in a simplified form that are further described below in the detailed description. This summary is not intended to identify key features or essential features of the claimed subject matter, nor is it intended to be used as an indication of the scope of the claimed subject matter.

Additional features and advantages of the disclosure will be set forth in the description which follows, and in part will be obvious from the description, or may be learned by the practice of the disclosure. The features and advantages of the disclosure may be realized and obtained by means of the instruments and combinations particularly pointed out in the appended claims. These and other features of the present disclosure will become more fully apparent from the following description and appended claims or may be learned by the practice of the disclosure as set forth hereinafter.

BRIEF DESCRIPTION OF THE DRAWINGS

In order to describe the manner in which the above recited and other advantages and features of the disclosure can be obtained, a more particular description of the disclosure briefly described above will be rendered by reference to specific embodiments thereof, which are illustrated in the appended drawings. It is appreciated that these drawings depict only typical embodiments of the disclosure and are not therefore to be considered to be limiting of its scope.

In the drawings, multiple instances of an element may each include separate letters appended to the element number. For example, two instances of a particular element "100" may be labeled as "100a" and "100b." In that case, the element label may be used without an appended letter (e.g., "100") to generally refer to every instance of the element, while the element label will include an appended letter (e.g., "100a") to refer to a specific instance of the element. Similarly, a drawing number may include separate letters appended thereto. For example, FIG. 2 may include FIG. 2A and FIG. 2B. In that case, the drawing number may be used without the appended letter (e.g., FIG. 2) to generally refer to every instance of the drawing, while the drawing label will include an appended letter (e.g., FIG. 2A) to refer to a specific instance of the drawing. The disclosure will be described and explained with additional specificity and detail through the use of the accompanying drawings in which.

DETAILED DESCRIPTION

Before describing various embodiments of the present disclosure in detail, it is to be understood that this disclosure is not limited to the parameters of the particularly exemplified systems, methods, apparatus, products, processes, and/or kits, which may, of course, vary. Thus, while certain embodiments of the present disclosure will be described in detail, with reference to specific configurations, parameters, components, elements, etc., the descriptions are illustrative and are not to be construed as limiting the scope of the claimed invention. In addition, the terminology used herein is for the purpose of describing the embodiments and is not necessarily intended to limit the scope of the claimed invention.

Furthermore, it is understood that for any given component or embodiment described herein, any of the possible candidates or alternatives listed for that component may generally be used individually or in combination with one another, unless implicitly or explicitly understood or stated otherwise. Additionally, it will be understood that any list of such candidates or alternatives is merely illustrative, not limiting, unless implicitly or explicitly understood or stated otherwise.

In addition, unless otherwise indicated, numbers expressing quantities, constituents, distances, or other measurements used in the specification and claims are to be understood as being modified by the term "about," as that term is defined herein. Accordingly, unless indicated to the contrary, the numerical parameters set forth in the specification and attached claims are approximations that may vary depending upon the desired properties sought to be obtained by the subject matter presented herein. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the subject matter presented herein are approximations, the numerical values set forth in the specific examples are reported as precisely as possible. Any numerical values, however, inherently contain certain errors necessarily resulting from the standard deviation found in their respective testing measurements.

Any headings and subheadings used herein are for organizational purposes only and are not meant to be used to limit the scope of the description or the claims.

Overview of Limb Elevation Devices

Figure 1:
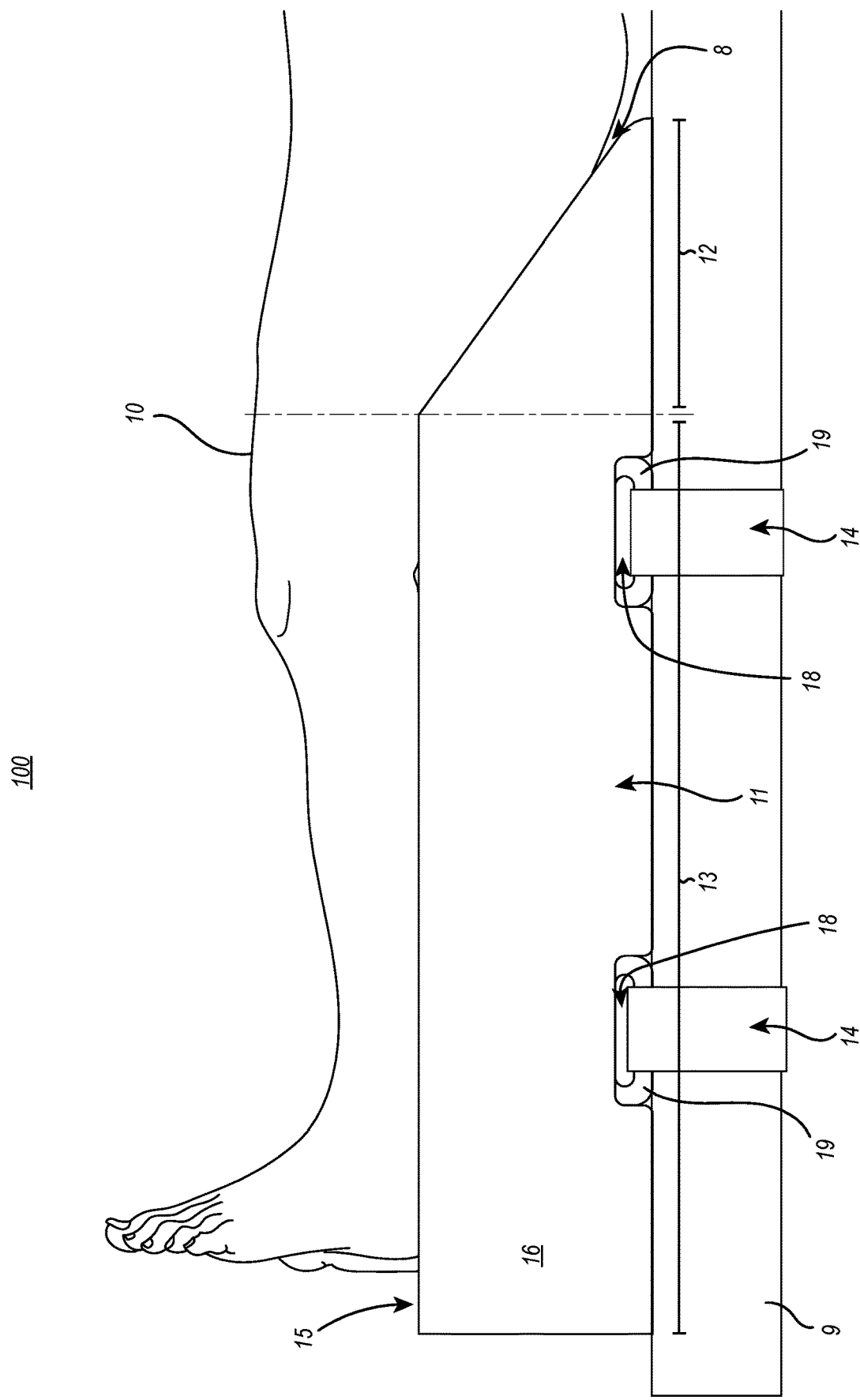
FIG. 1 illustrates exemplary use of a limb elevation device according to one or more embodiments of the present disclosure.

FIG. 1 illustrates an exemplary limb elevation device 100 supporting and elevating a patient's leg 10. The limb elevation device 100 may comprise a base 11 having a proximal section 12 and a distal section 13 and one or more securement straps 14. The securement straps 14 may be selectively attached to the base 11 in various configurations based on user preference or need to accommodate specific injuries or conditions. The securement straps 14 may be used to secure the limb elevation device 100 to a surface 9. The surface 9 may be a location for a medical procedure, such as a surgical table, or a pre- or post-operative location such as a hospital bed or physical therapy apparatus. The example embodiment shown in FIG. 1 features elevation of a patient's leg 10, however, the device may be configured to support different limbs or extremities as needed.

Figure 2:
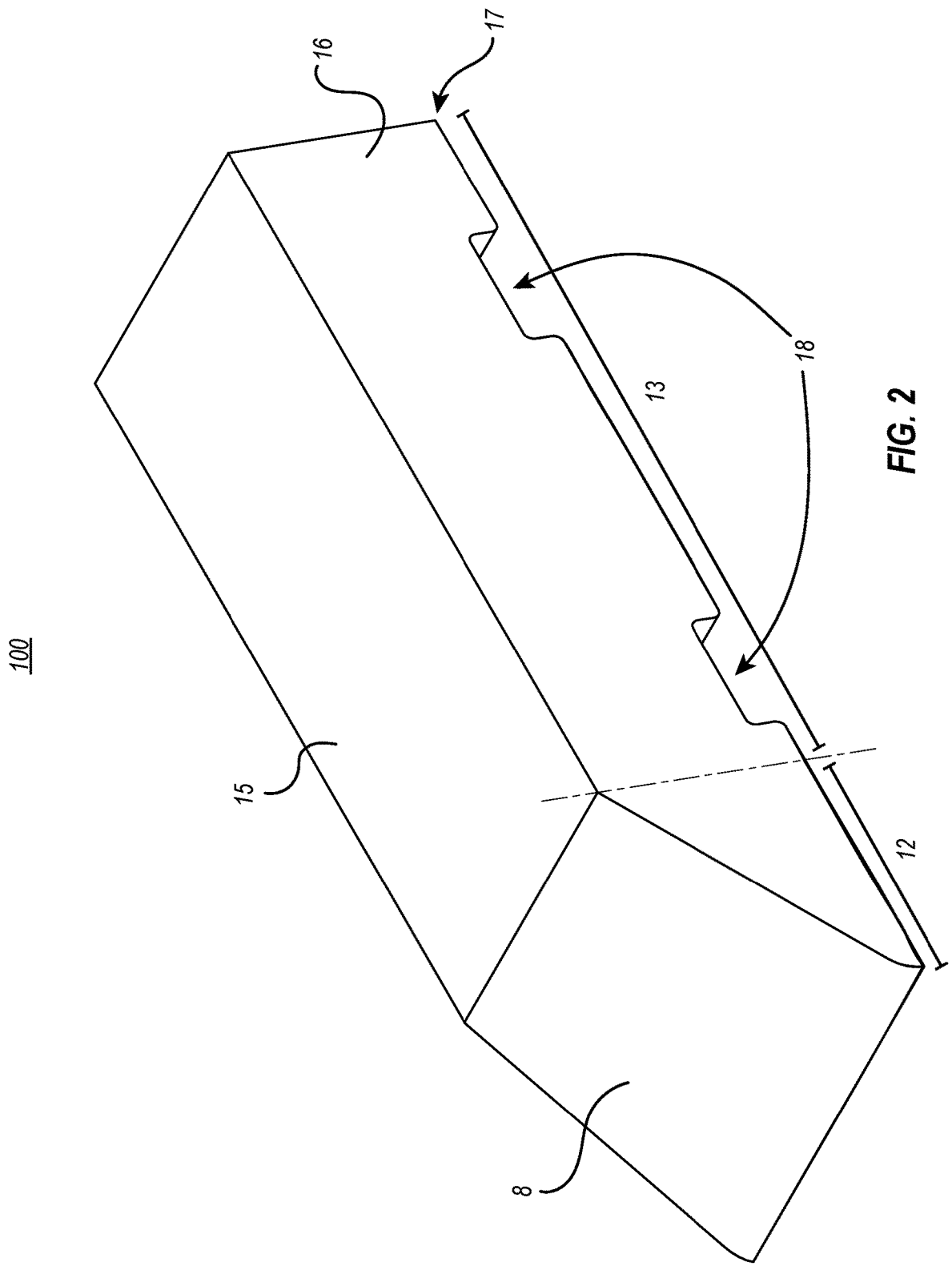
FIG. 2 illustrates an example of a base of a limb elevation device according to one or more embodiments of the present disclosure.

FIG. 2 illustrates the base 11 of the limb elevation device 100. The proximal section 12 of the base 11 may have a sloped, inclined, or angled upper surface 8, and may comprise at least about 5%, 10%, 12%, 15%, 18%, 20%, 23%, 25%, 28%, 30%, 35%, or 40% of the total length of the base 11, or may have a length that is a percentage of the total length of the base 11 within a range having endpoints selected from any two of the foregoing percentages.

The base 11 may have an overall height (at the highest planar surface) of about 4.5 inches, about 5 inches, about 5.5 inches, about 6 inches, about 6.5 inches, about 7 inches, about 7.5 inches, about 8 inches, about 8.5 inches, about 9 inches, about 9.5 inches, or about 10 inches, or a height within a range with endpoints selected from any two of the foregoing values. The base may have an overall length of about 24 inches, about 27 inches, about 30 inches, about 33 inches, about 36 inches, about 39 inches, or about 42 inches, or a length within a range with endpoints selected from any two of the foregoing values.

The proximal section 12 may serve as a wedge or a ramp to gradually elevate a limb. The proximal section 12 may provide support to a limb as it is elevated. The support provided by the angled upper surface 8 of the proximal section 12 may advantageously prevent fatigue and discomfort when a limb is elevated for an extended period of time. The proximal section 12 may be placed underneath the base of the limb, or the portion of the limb closest to the center of the patient's body.

The distal section 13 may have a flat or planar upper surface 15 with opposing sidewalls 16 extending downward to a bottom surface 17. The total length of the distal section 13 may be dictated by the length of the limb to be elevated. The bottom surface 17 of the distal section 13 may have at least one recess 18 extending transversely across the bottom surface 17 through the opposing sidewalls 16. The width of the recess may depend on the width of the securement straps 14. Recesses having widths of about 1 to about 3 inches have been found to function effectively.

Figure 3:
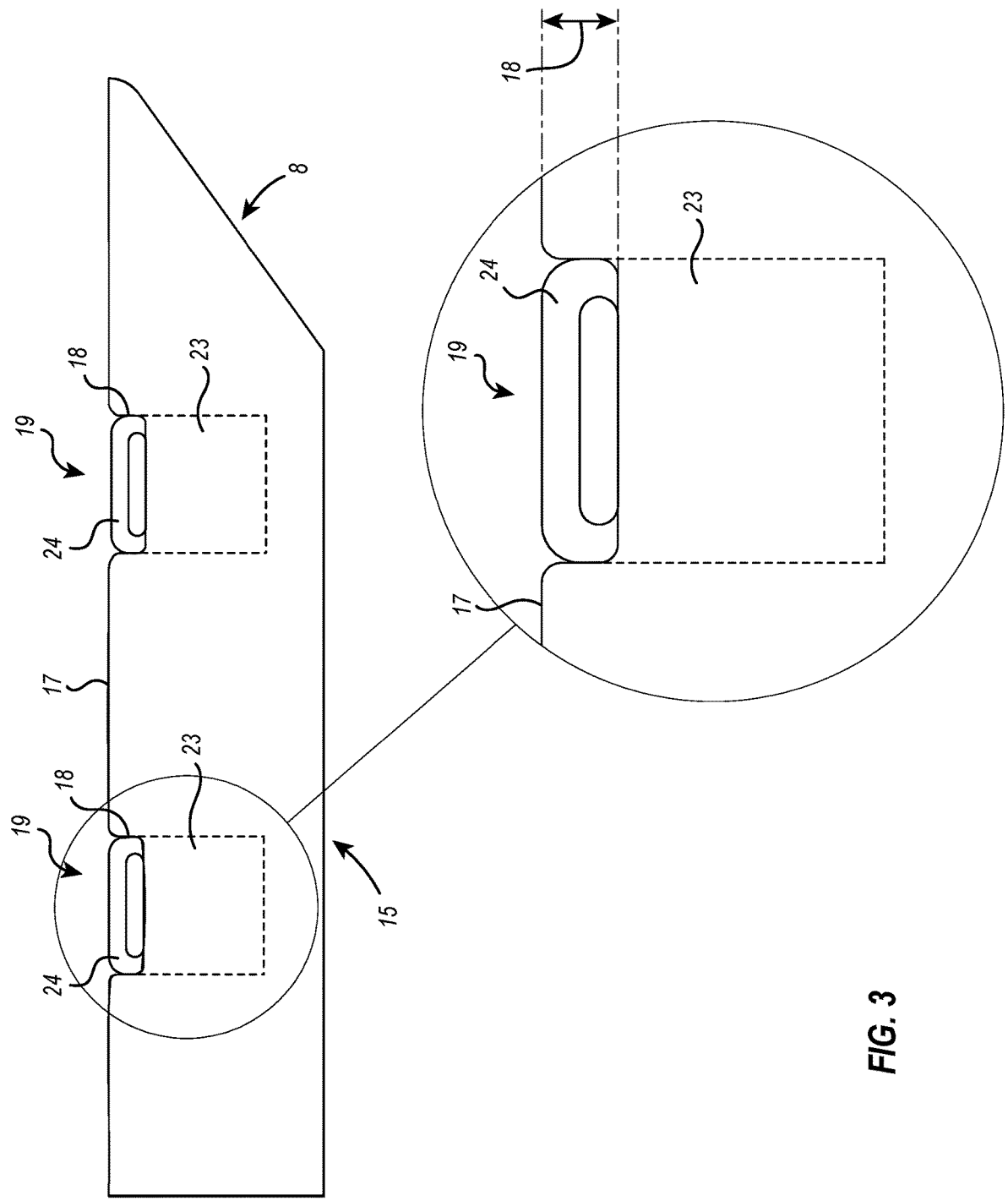
FIG. 3 illustrates a base of a limb elevation device turned upside down to display the bottom surface according to one or more embodiments of the present disclosure.

Turning now to FIG. 3, one or more anchor points 19 may be disposed within each recess 18. The anchor points 19 may be configured to accommodate the width of a securement strap 14. The anchor points 19 may comprise a hook, loop, buckle, hitch, or similar fastening point. The anchor points 19 may be formed of substantially rigid materials such as metal or hard plastics which may provide stability and support to the limb elevation device when in use in addition to providing a secure structure for attachment of a corresponding strap and for distributing forces applied via the straps so that the material (e.g., foam) of the base itself is not sheared or otherwise ruined.

In some embodiments, the anchor points 19 may has radiolucent properties and may be formed of materials such as thermoplastic polymers, for example, acrylonitrile butadiene styrene (ABS) or high-density polyethylene (HDPE) plastic. Furthermore, the substantially rigid materials forming the anchor points 19 may allow the securement straps 14 to be fastened securely to a surface 9 without overextending and displacing the anchor point 19.

The anchor points 19 may each include an exposed end 24 which may be visible when fixed within the recess 18, and a stabilizing end 23 fixed within the base 11 and not visible when the limb elevation device 100 is assembled. The stabilizing end 23 may provide additional support when the securement straps 14 are selectively secured to a surface 9. The anchor points 19 may not extend out of the recess 18 beyond the level of the bottom surface 17 of the distal section 13 of the base 11. In other words, the height of the exposed end 24 of the anchor point 19 may terminate before or at the bottom surface 17 providing a continuous or even "flush" bottom surface 17 for stability.

Figure 4A:
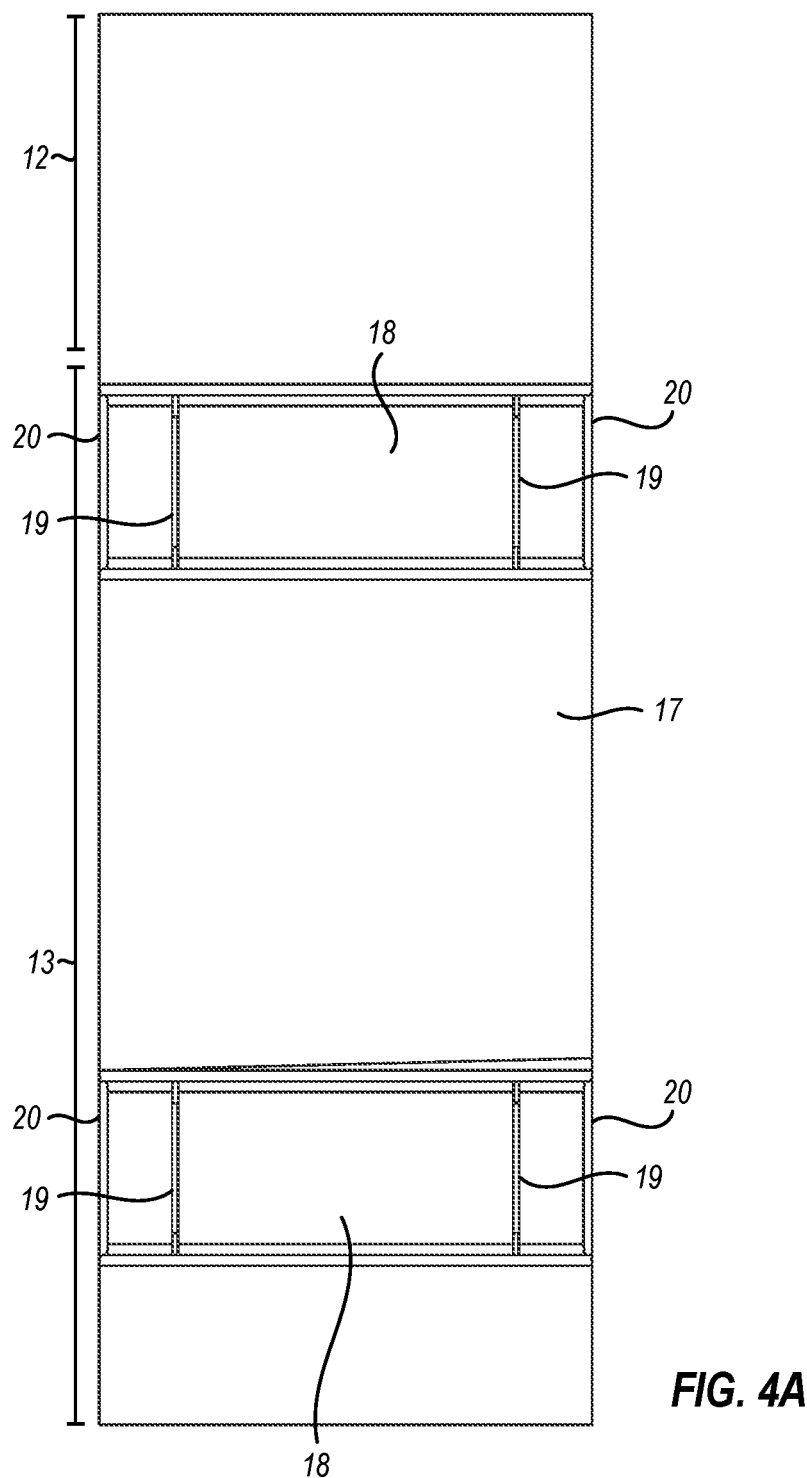
FIGS. 4A and 4B illustrate a detail view of a recess on the bottom surface of a base of a limb elevation device according to one or more embodiments of the present disclosure.
Figure 4B:
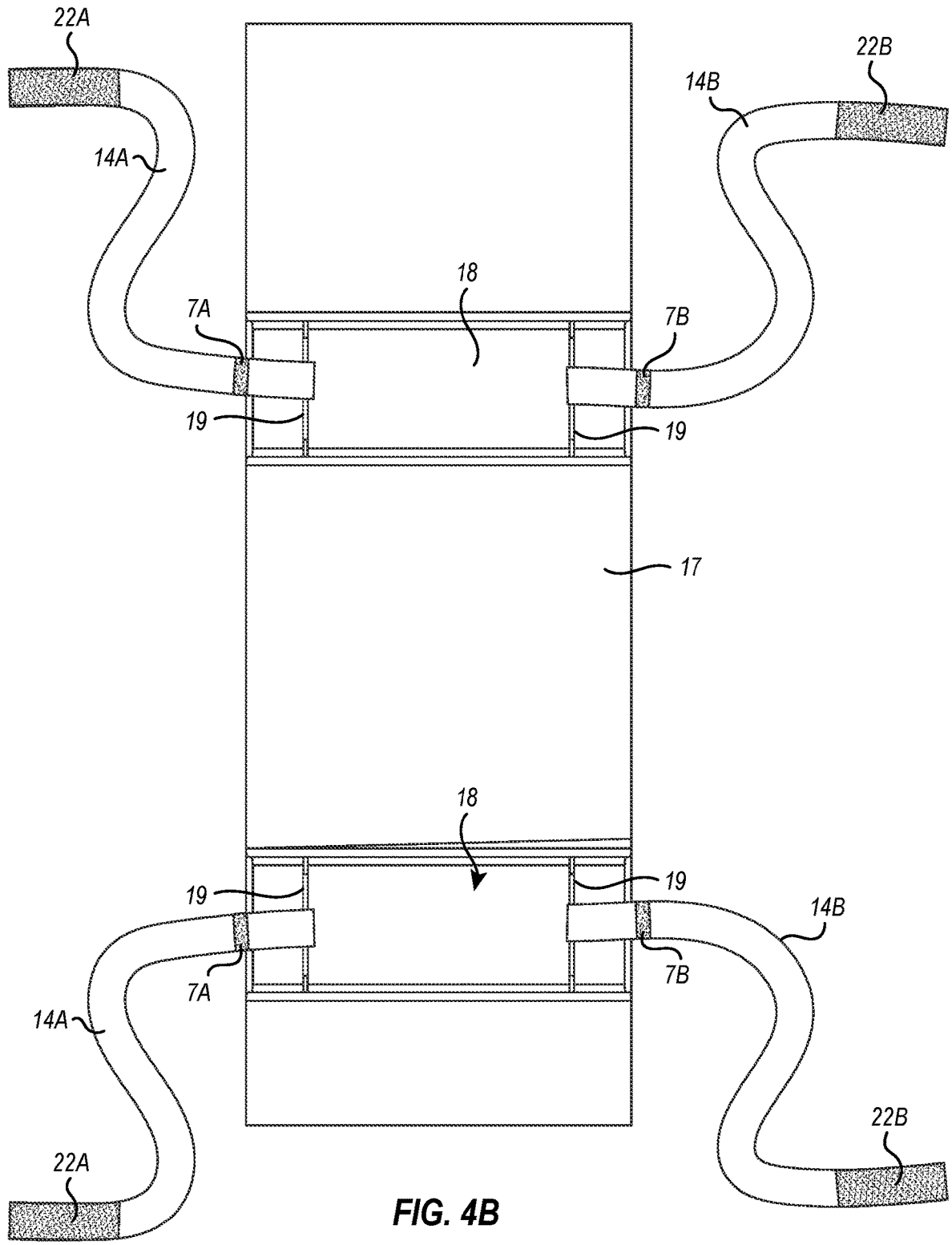

FIG. 4A illustrates an example of the recess 18 in the bottom surface 17 of the distal section 13 of the base 11 of the limb elevation device 100. In some embodiments, it may be preferred to have the anchor points 19 set inside of the edge 20 of the recess for added stability. A strap 14A, 14B may be attached to an anchor point 19 as shown in FIG. 4B. A securing end 7A, 7B of the strap 14A, 14B may be attached to an anchor point 19 using hook and loop fasteners, clips, snaps, buttons, buckles or the like. In some embodiments, the securement straps 14A, 14B may include corresponding fasteners so that a securing end 22A of a first securement strap 14A may be selectively attached to a complementary securing end 22B of a second securement strap 14B when the securement straps are selectively secured to a surface 9.

Figure 5A:
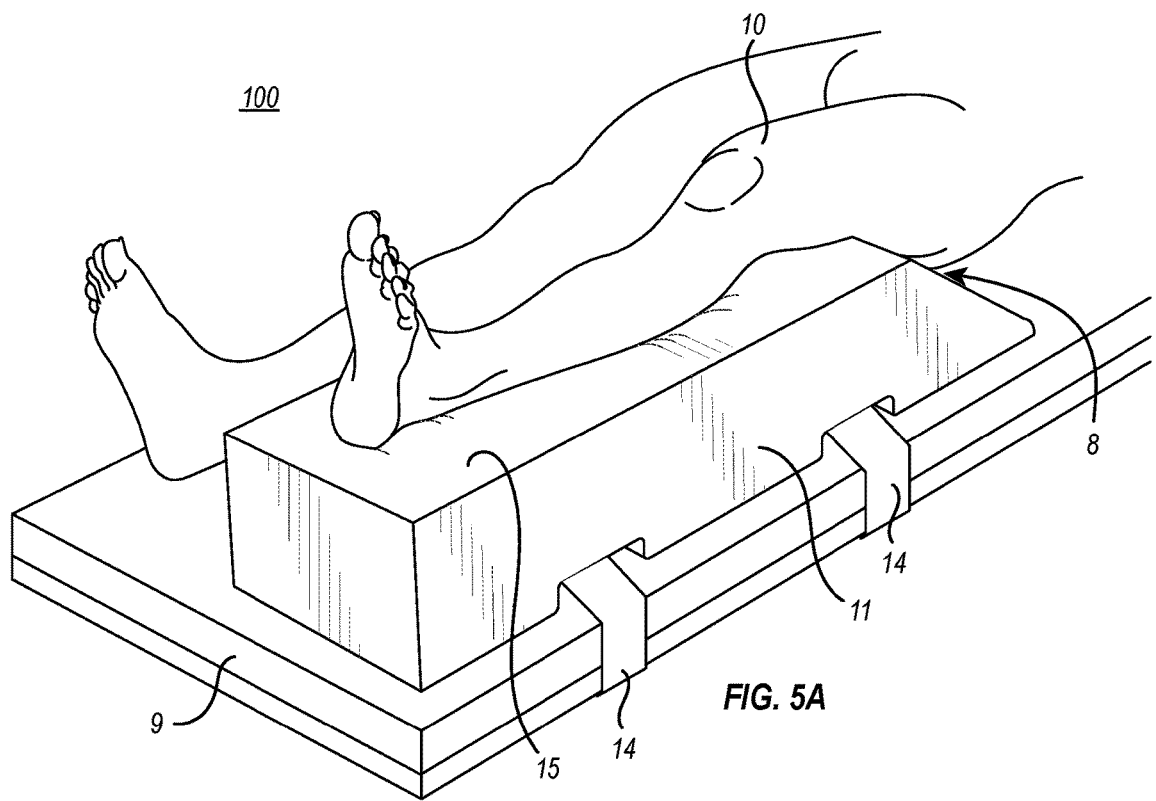
FIGS. 5A and 5B illustrate examples of top plan views of strap configurations securing a limb elevation device to a surface according to one or more embodiments of the present disclosure.
Figure 5B:
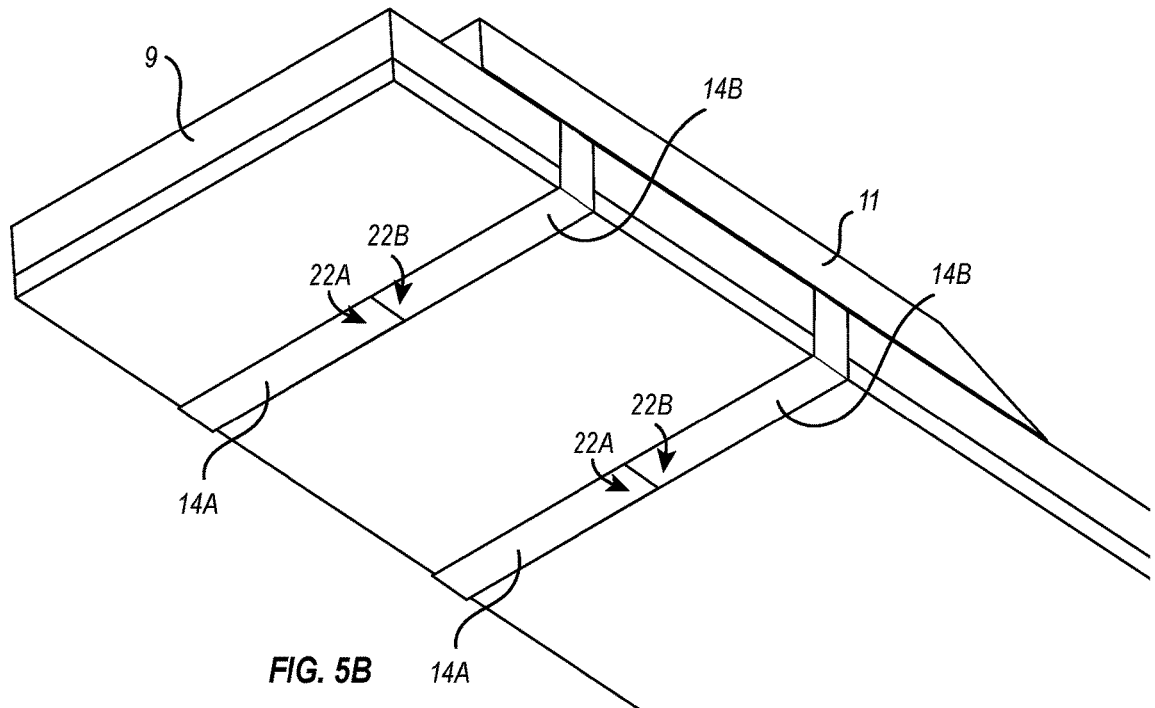

FIGS. 5A and 5B illustrate an example of a limb elevation device 100 selectively attached to a surface 9. The straps 14 may be used to secure the base 11 to the surface 9 by selectively attaching the first securement strap 14A to the second securement strap 14B via the corresponding fasteners of securing end 22A and 22B.

Figure 6A:
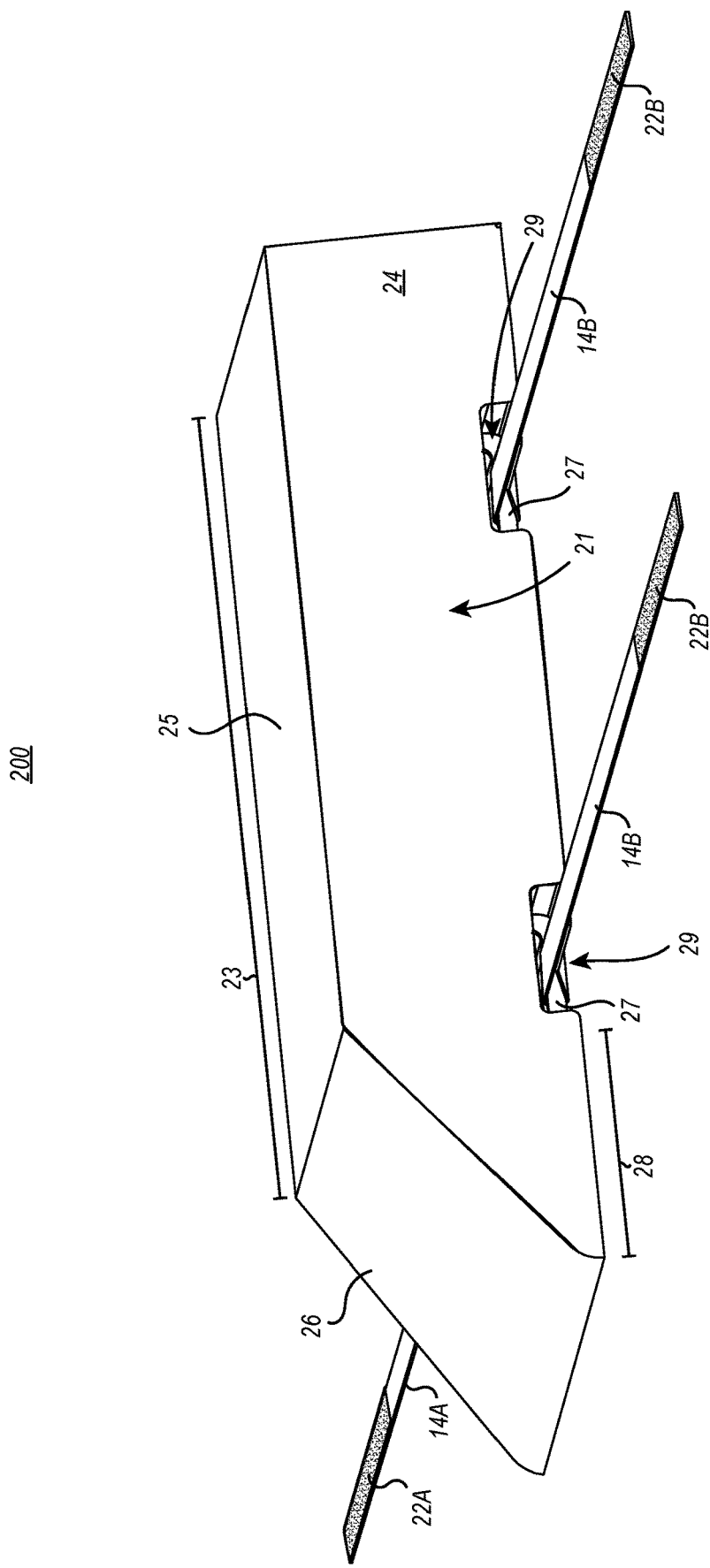
FIGS. 6A and 6B illustrate a limb elevation device according to one or more embodiments of the present disclosure.
Figure 6B:
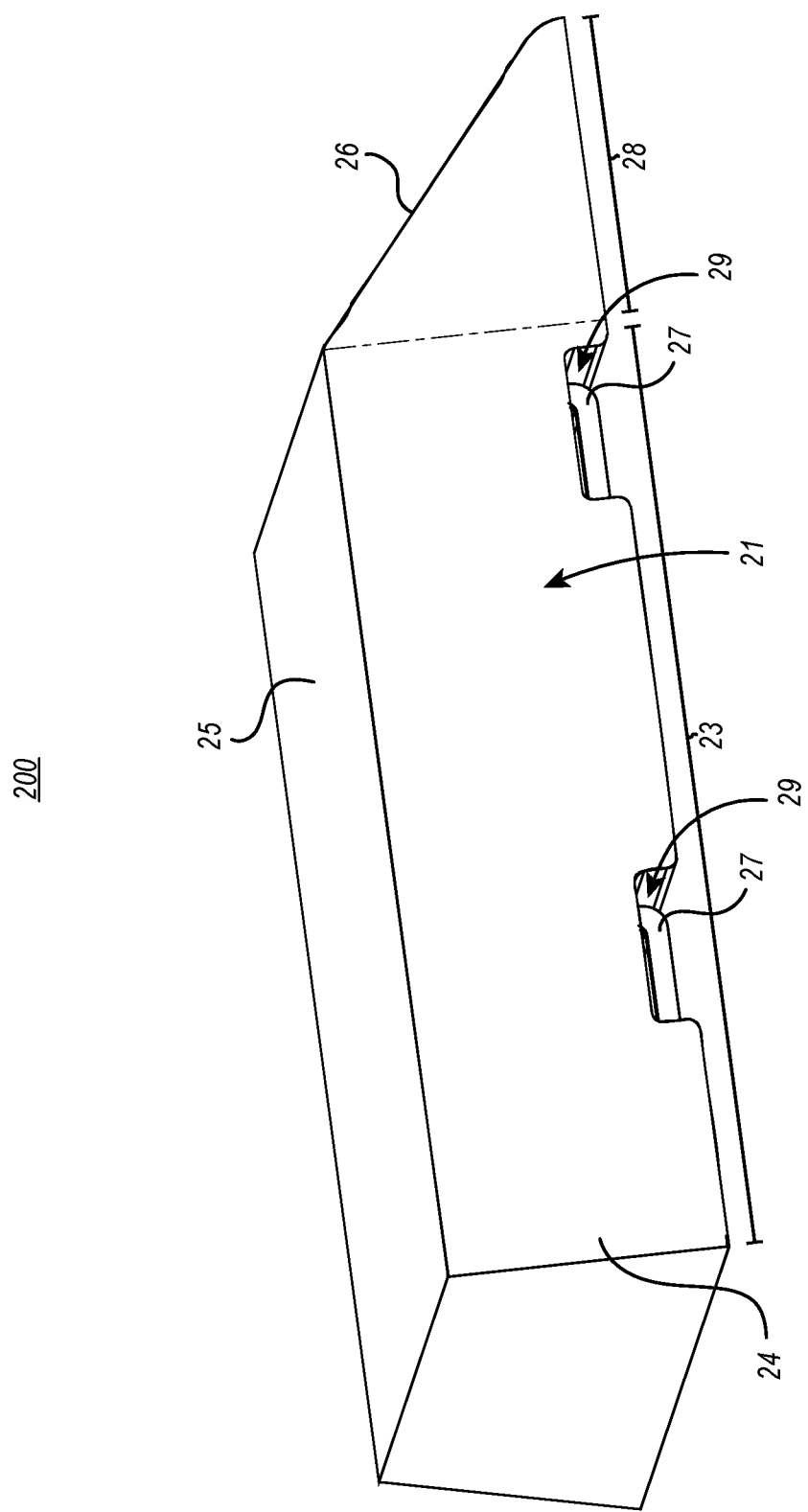

In another embodiment of a limb elevation device 200, as shown in FIGS. 6A-6B, the opposing sidewalls 24 of the base 21 may extend downward from the upper surface 25 of the distal section 23 of the base 21 at an angle. The angled opposing sidewalls 24 may be advantageous in providing added stability to the limb elevation device. This may be desirable on soft or uneven surfaces such as on hospital beds. The distal section 23 of the base 21 may include a substantially flat or planar upper surface 25 and may include one or more anchor points 27 disposed within a recess 29 on the bottom surface of the distal section 23. The proximal section 22 of the limb elevation device 200 may include a sloped or inclined upper surface 26 forming a ramp providing for the gradual elevation of a limb placed thereon. Securement straps 28 may be selectively attached to the anchor points and selectively secured to a surface 9 as shown above in FIGS. 5A and 5B.

Figure 7A:
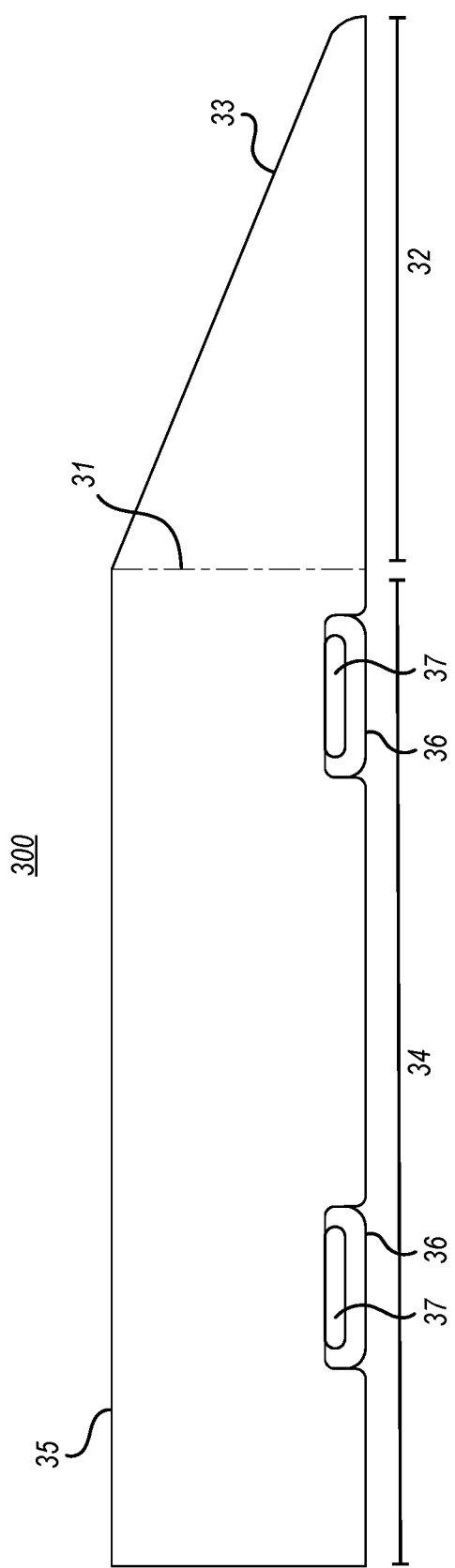
FIGS. 7A and 7B illustrate a limb elevation device according to one or more embodiments of the present disclosure.

In another embodiment, a limb elevation device 300, as illustrated in FIG. 7A, may include a base 31 having a proximal section 32 and a distal section 34. The proximal section 32 may include a sloped or inclined upper surface 33, and the distal section may include a substantially flat or planar upper surface 35. The distal section 34 may include one or more anchor points 36 disposed within one or more recesses 37 of the bottom surface of the distal section 34. The proximal section 32 may comprise 20%-45% of the total length of the base, more preferably 25%-40% of the total length of the base, more preferably 30%-40% of the total length of the base.

Figure 7B:
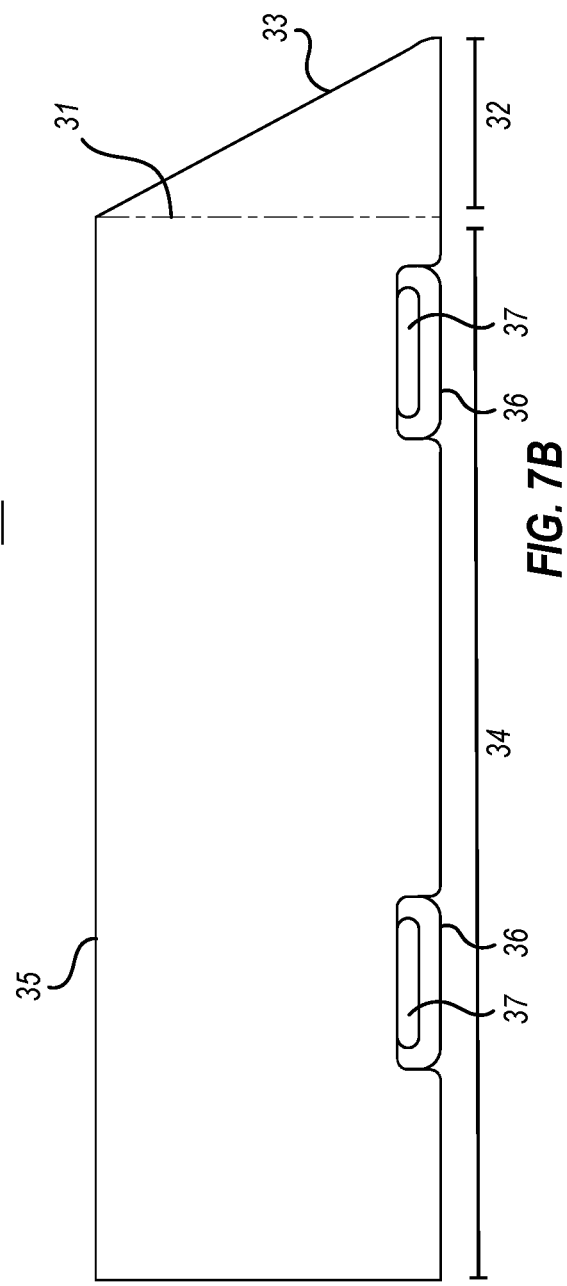

FIG. 7B illustrates another embodiment of a limb elevation device 300, where the proximal section 32 is shortened to create a steeper angle for the inclined or sloped upper surface 33 of the proximal section 32. Where the proximal section is shortened relative to the distal section 34, the proximal section 32 may comprise 2%-10% of the total length of the base 31, more preferably 3%-8% of the total length of the base, more preferably 4%-6% of the total length of the base. The angle of the inclined upper surface of the proximal section may depend on the preferred course of treatment. For example, some injuries may require that a limb be elevated at a steep angle (i.e. an angle greater than 45°), while others may require a moderate or gradual angle (i.e. an angle less than 45°.

Figure 8A:
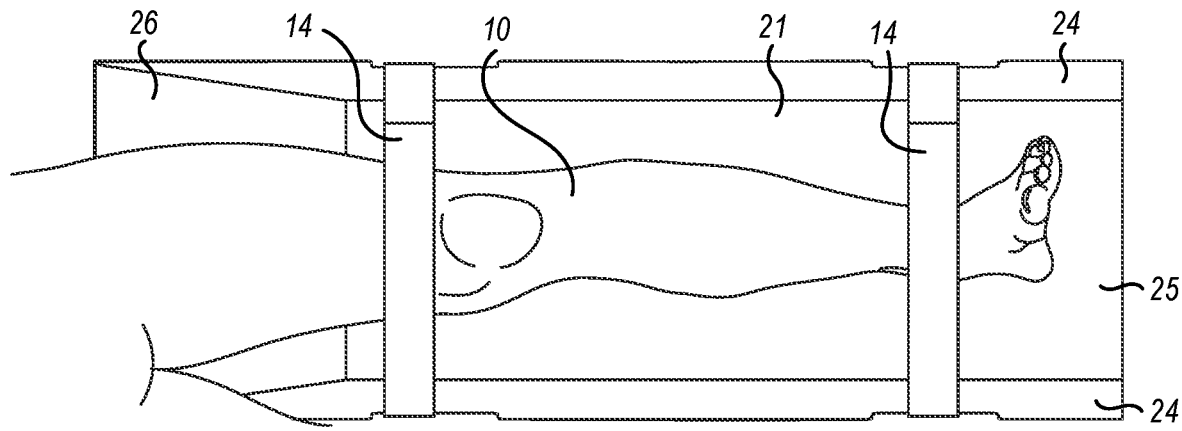
FIGS. 8A-8C illustrate examples of an additional securing feature of a limb elevation device according to one or more embodiments of the present disclosure.
Figure 8B:
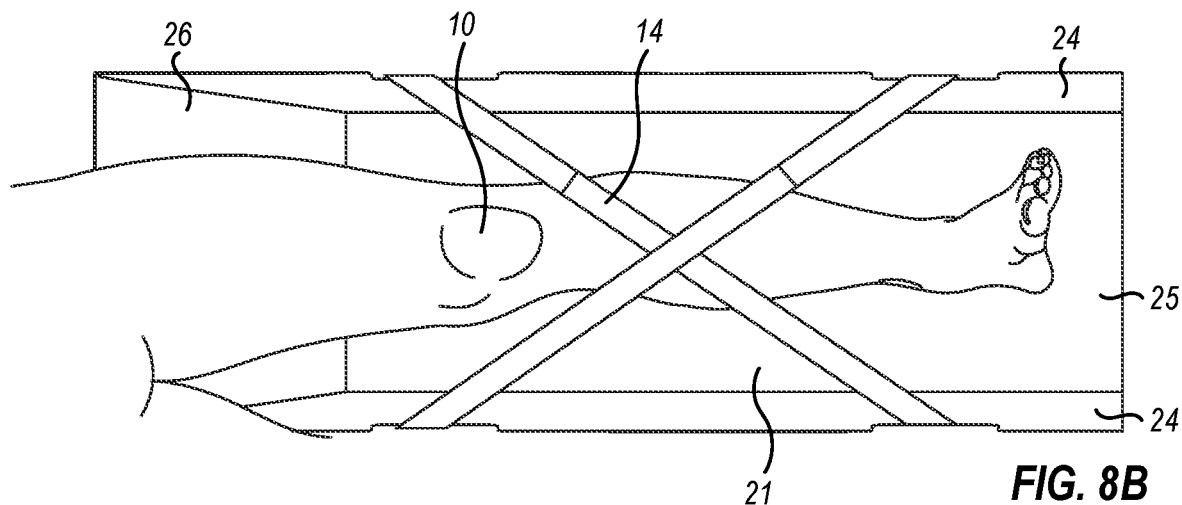
Figure 8C:
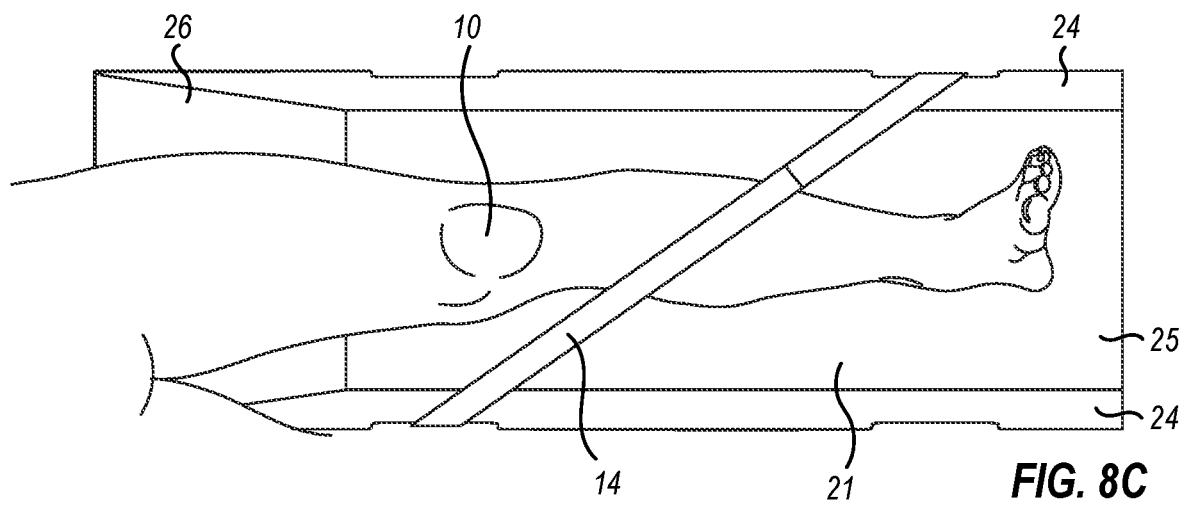

FIGS. 8A-8C demonstrate an additional or alternative use of the securement straps 14 of embodiments of limb elevation devices 100, 200, 300 as described above. In FIGS. 8A-8C, the embodiment shown is limb elevation device 200, though this additional use of the securement straps 14 may be incorporated into any of the embodiments described above. In some embodiments, the securement straps 14 may also be used to secure a leg 10 in position on the upper surface 25 of the base 21 of a limb elevation device 200. The securement straps 14 may be positioned in various configurations to achieve the preferred securing effect. The configuration of the securement straps may depend, for example, on the injury or procedure performed on the leg 10.

The additional use of the securement straps 14 to secure a leg 10 may be advantageous in situations where a patient may first have a procedure performed on a leg 10. During the procedure, the limb elevation device 200 may be secured to a surface 9 such as a surgical table. Once the surgery is complete, the straps 14 may be removed from the surface and secured over the leg 10 in order to maintain the leg 10 in an elevated position post-surgery. This may allow patients to be moved while maintaining the limb in an elevated position.

The limb elevation device of the various embodiments described above may be formed of a foam polymer material. The foam polymer material may be optionally coated with a water-impermeable polymer (e.g., vinyl-based) to protect the foam and provide for easier cleaning. The polymer foam may cushion the limb and provide the user with a comfortable experience when the limb of the user is secured on the limb elevation device for an extended period of time. The foam polymer may cushion the limb while maintaining the limb on the top surface of the base. In other words, the limb may not sink into the foam and cover the sides of the limb. This may be advantageous in situations where medical professionals or caregivers need to access the side of a limb to assess wounds or provide treatment. Users may also prefer this configuration to provide more airflow to the sides of the limb.

Unless defined otherwise, all technical and scientific terms used herein have the same meaning as commonly understood by one of ordinary skill in the art to which the present disclosure pertains.

Various aspects of the present disclosure, including devices, systems, and methods may be illustrated with reference to one or more embodiments or implementations, which are exemplary in nature. As used herein, the term "exemplary" means "serving as an example, instance, or illustration," and should not necessarily be construed as preferred or advantageous over other embodiments disclosed herein. In addition, reference to an "implementation" of the present disclosure or invention includes a specific reference to one or more embodiments thereof, and vice versa, and is intended to provide illustrative examples without limiting the scope of the invention, which is indicated by the appended claims rather than by the following description.

As used throughout this application the words "can" and "may" are used in a permissive sense (i.e., meaning having the potential to), rather than the mandatory sense (i.e., meaning must). Additionally, the terms "including," "having," "involving," "containing," "characterized by," as well as variants thereof (e.g., "includes," "has," "involves," "contains," etc.), and similar terms as used herein, including within the claims, shall be inclusive and/or open-ended, shall have the same meaning as the word "comprising" and variants thereof (e.g., "comprise" and "comprises"), and do not exclude additional un-recited elements or method steps, illustratively.

It will be noted that, as used in this specification and the appended claims, the singular forms "a," "an" and "the" include plural referents unless the context clearly dictates otherwise. Thus, for example, reference to a singular referent (e.g., "widget") includes one, two, or more referents. Similarly, reference to a plurality of referents should be interpreted as comprising a single referent and/or a plurality of referents unless the content and/or context clearly dictate otherwise. For example, reference to referents in the plural form (e.g., "widgets") does not necessarily require a plurality of such referents. Instead, it will be appreciated that independent of the inferred number of referents, one or more referents are contemplated herein unless stated otherwise.

As used herein, directional terms, such as "top," "bottom," "left," "right," "up," "down," "upper," "lower," "proximal," "distal" and the like are used herein solely to indicate relative directions and are not otherwise intended to limit the scope of the disclosure and/or claimed invention.

Specific language will be used herein to describe the exemplary embodiments. Nevertheless, it will be understood that no limitation of the scope of the disclosure is thereby intended. Rather, it is to be understood that the language used to describe the exemplary embodiments is illustrative only and is not to be construed as limiting the scope of the disclosure (unless such language is expressly described herein as essential).

Any headings used herein are for organizational purposes only and are not meant to be used to limit the scope of the description or the claims.

Various aspects of the present disclosure can be illustrated by describing components that are bound, coupled, attached, connected, and/or joined together. As used herein, the terms "bound," "coupled", "attached", "connected," and/or "joined" are used to indicate either a direct association between two components or, where appropriate, an indirect association with one another through intervening or intermediate components. In contrast, when a component is referred to as being "directly bound," "directly coupled", "directly attached", "directly connected," and/or "directly joined" to another component, no intervening elements are present or contemplated. Furthermore, binding, coupling, attaching, connecting, and/or joining can comprise mechanical and/or chemical association.

Conclusion

Various alterations and/or modifications of the inventive features illustrated herein, and additional applications of the principles illustrated herein, which would occur to one skilled in the relevant art and having possession of this disclosure, can be made to the illustrated embodiments without departing from the spirit and scope of the invention as defined by the claims, and are to be considered within the scope of this disclosure. Thus, while various aspects and embodiments have been disclosed herein, other aspects and embodiments are contemplated. While a number of methods and components similar or equivalent to those described herein can be used to practice embodiments of the present disclosure, only certain components and methods are described herein.

It will also be appreciated that systems, devices, products, kits, methods, and/or processes, according to certain embodiments of the present disclosure may include, incorporate, or otherwise comprise properties, features (e.g., components, members, elements, parts, and/or portions) described in other embodiments disclosed and/or described herein. Accordingly, the various features of certain embodiments can be compatible with, combined with, included in, and/or incorporated into other embodiments of the present disclosure. Thus, disclosure of certain features relative to a specific embodiment of the present disclosure should not be construed as limiting application or inclusion of said features to the specific embodiment. Rather, it will be appreciated that other embodiments can also include said features, members, elements, parts, and/or portions without necessarily departing from the scope of the present disclosure.

Moreover, unless a feature is described as requiring another feature in combination therewith, any feature herein may be combined with any other feature of a same or different embodiment disclosed herein. Furthermore, various well-known aspects of illustrative systems, methods, apparatus, and the like are not described herein in particular detail in order to avoid obscuring aspects of the example embodiments. Such aspects are, however, also contemplated herein.

The present disclosure may be embodied in other specific forms without departing from its spirit or essential characteristics. The described embodiments are to be considered in all respects only as illustrative and not restrictive. The scope of the invention is, therefore, indicated by the appended claims rather than by the foregoing description. While certain embodiments and details have been included herein and in the attached disclosure for purposes of illustrating embodiments of the present disclosure, it will be apparent to those skilled in the art that various changes in the methods, products, devices, and apparatus disclosed herein may be made without departing from the scope of the disclosure or of the invention, which is defined in the appended claims. All changes which come within the meaning and range of equivalency of the claims are to be embraced within their scope.

What is claimed is:

1. A limb elevation device, comprising:
   a base, the base including a proximal section and a distal section, each of the proximal section and distal section including:
   a bottom surface extending along a longitudinal axis,
   side surfaces extending upward from the bottom surface, and
   an upper surface,
   wherein the upper surface of the proximal section of the base is inclined,
   wherein the upper surface of the distal section of the base is planar,
   wherein the bottom surface of the distal section has at least one recess; and
   a plurality of anchor points positioned within the at least one recess, wherein each anchor point is disposed near a lateral end of the at least one recess near a respective side surface but inset from the respective side surface.

2. The limb elevation device of claim 1, further comprising at least one securement strap attached to the at least one anchor point.

3. The limb elevation device of claim 2, wherein the at least one securement strap is selectively removable and repositionable on the base.

4. The limb elevation device of claim 2, comprising a plurality of securement straps, wherein each securement strap has an attachment end and a securing end, and wherein the attachment end is selectively connected to the at least one anchor point, the securing end being free to engage with and secure to another securing end of another securement strap.

5. The limb elevation device of claim 1, wherein the at least one anchor point extends no lower than the bottom surface of the distal section.

6. The limb elevation device of claim 5, wherein the at least one anchor point is substantially flush with the bottom surface of the distal section.

7. The limb elevation device as in claim 1, wherein the at least one recess extends transversely across the bottom surface of the distal section.

8. The limb elevation device of claim 1, wherein the at least one anchor point is rigid.

9. The limb elevation device of claim 1, wherein a separate securement strap is associated with each of the anchor points.

10. The limb elevation device of claim 1, wherein the distal section constitutes about 60% to about 90% of the length of the base.

11. The limb elevation device of claim 1, wherein the proximal section constitutes about 5% to about 15% of the length of the base.

12. The limb elevation device of claim 1, wherein the base is formed of a foam material coated with a water-impermeable polymer.

13. A limb elevation device, comprising:
 a base, the base including a proximal section and a distal section, each of the proximal section and distal section including:
  a bottom surface extending along a longitudinal axis and configured to be placed onto a patient limb supporting surface,
  a recess in and extending transversely across the bottom surface,
  side surfaces extending upward from the bottom surface, and
  an upper surface configured for placement of a patient's limb thereon, wherein the upper surface of the proximal section of the base is inclined and the upper surface of the distal section of the base is planar; and
 at least two rigid anchor points positioned within the recess in the bottom surface.

14. The limb elevation device of claim 13, further comprising a securement strap attached to each of the rigid anchor points.

15. The limb elevation device of claim 13, wherein each anchor point is disposed near a lateral end of the recess near a respective side surface but inset from the respective side surface.

16. The limb elevation device of claim 13, wherein the at least two rigid anchor points are substantially flush with the bottom surface of the distal section.

17. The limb elevation device of claim 13, wherein the side surfaces extend downward from the upper surface of the distal section of the base at an angle.

18. A limb elevation device, comprising:
 a base, the base including a proximal section and a distal section, each of the proximal section and distal section including:
  a bottom surface extending along a longitudinal axis,
  a first recess in the bottom surface of the distal section,
  a second recess in the bottom surface of the proximal section,
  side surfaces extending upward from the bottom surface, and
  an upper surface, wherein the upper surface of the proximal section of the base is inclined and the upper surface of the distal section of the base is planar; and
 at least two rigid anchor points positioned within each of the first and second recesses, wherein each anchor point is disposed near a lateral end of its corresponding recess near a respective side surface but inset from the respective side surface.

19. The limb elevation device of claim 18, further comprising a securement strap attached to each rigid anchor point.

20. A limb elevation device, comprising:
 a base, the base including a proximal section configured to be placed underneath a base portion of the limb closest to a center of a patient's body and a distal section configured to be placed underneath a portion of the limb that extends distally from the base portion of the limb, each of the proximal section and distal section including:
  a bottom surface extending along a longitudinal axis and configured to be placed onto a patient limb supporting surface,
  a recess in and extending transversely across the bottom surface,
  side surfaces extending upward from the bottom surface, and
  an upper surface, wherein the upper surface of the proximal section of the base is inclined to provide a ramp for the base portion of the limb and the upper surface of the distal section of the base is planar and elevated relative to the ramp provided by the proximal section; and
 at least one rigid anchor point positioned within the recess in the bottom surface.

* * * * *